United States Patent
Hall et al.

(10) Patent No.: US 9,468,413 B2
(45) Date of Patent: Oct. 18, 2016

(54) METHOD AND APPARATUS FOR CATHETER GUIDANCE USING A COMBINATION OF ULTRASOUND AND X-RAY IMAGING

(71) Applicant: General Electric Company, Schenectady, NY (US)

(72) Inventors: Anne Lindsay Hall, Schenectady, NY (US); Michael Washburn, Schenectady, NY (US); William Alphonsus Zang, Schenectady, NY (US)

(73) Assignee: General Electric Company, Schenectady, NY (US)

(*) Notice: Subject to any disclaimer, the term of this patent is extended or adjusted under 35 U.S.C. 154(b) by 0 days.

(21) Appl. No.: 14/721,145

(22) Filed: May 26, 2015

(65) Prior Publication Data

US 2015/0250434 A1    Sep. 10, 2015

Related U.S. Application Data

(62) Division of application No. 12/205,599, filed on Sep. 5, 2008, now abandoned.

(51) Int. Cl.
*A61B 6/12* (2006.01)
*A61B 6/00* (2006.01)
(Continued)

(52) U.S. Cl.
CPC .............. *A61B 6/12* (2013.01); *A61B 6/4417* (2013.01); *A61B 6/463* (2013.01); *A61B 6/464* (2013.01);
(Continued)

(58) Field of Classification Search
CPC ...... A61B 6/12; A61B 6/4417; A61B 6/463; A61B 6/464; A61B 6/469; A61B 6/481; A61B 6/504; A61B 6/5247; A61B 8/0833; A61B 8/0841; A61B 8/0891; A61B 8/4254; A61B 8/4416; A61B 8/463; A61B 8/464; A61B 8/469; A61B 8/481; A61B 8/483; A61B 8/5238; A61B 8/5261; A61B 8/14; A61B 19/5244; A61B 8/4472; A61B 2019/5238; A61B 2019/5276; A61M 25/09
See application file for complete search history.

(56) References Cited

U.S. PATENT DOCUMENTS 5,203,337 A    4/1993   Feldman
5,391,199 A    2/1995   Ben-Haim
(Continued)

FOREIGN PATENT DOCUMENTS

DE    10340546    3/2005
EP     1637070    3/2005
(Continued)

OTHER PUBLICATIONS

Zhang et al., Electromagnetic tracking for abdominal interventions in computer aided surgery, Comput Aided Surg. May 2006; 11(3): 127-136.*

(Continued)

*Primary Examiner* — Bo J Peng
(74) *Attorney, Agent, or Firm* — Dean D. Small; The Small Patent Law Group, LLC (57) ABSTRACT

An apparatus for tracking movement of a foreign object within a subject has an X-ray fluoroscopic system with an X-ray detector and an ultrasound system that has a probe with a position sensor. A display is configured to display a static X-ray image acquired by the X-ray fluoroscopic system and a real-time ultrasound image acquired by the ultrasound system. The X-ray image and the ultrasound image each display at least a portion of the foreign object and at least a portion of surrounding area. A tracking module is configured to track movement of the foreign object within the ultrasound image and the display is further configured to display an indication of the movement of the foreign object on the X-ray image.

20 Claims, 5 Drawing Sheets

(51) Int. Cl.
  *A61B 8/08* (2006.01)
  *A61B 8/00* (2006.01)
  *A61M 25/09* (2006.01)
  *A61B 8/14* (2006.01)

(52) U.S. Cl.
  CPC .............. *A61B 6/469* (2013.01); *A61B 6/481* (2013.01); *A61B 6/504* (2013.01); *A61B 6/5247* (2013.01); *A61B 8/0833* (2013.01); *A61B 8/0841* (2013.01); *A61B 8/0891* (2013.01); *A61B 8/4254* (2013.01); *A61B 8/4416* (2013.01); *A61B 8/463* (2013.01); *A61B 8/464* (2013.01); *A61B 8/469* (2013.01); *A61B 8/481* (2013.01); *A61B 8/483* (2013.01); *A61B 8/5238* (2013.01); *A61B 8/5261* (2013.01); *A61B 34/20* (2016.02); *A61M 25/09* (2013.01); *A61B 8/14* (2013.01); *A61B 8/4472* (2013.01); *A61B 2090/376* (2016.02); *A61B 2090/378* (2016.02)

(56) References Cited

U.S. PATENT DOCUMENTS

| | | | |
|---|---|---|---|
| 5,409,000 | A | 4/1995 | Imran |
| 5,409,007 | A | 4/1995 | Saunders et al. |
| 5,432,544 | A | 7/1995 | Ziarati |
| 5,438,997 | A | 8/1995 | Sieben et al. |
| 5,568,809 | A | 10/1996 | Ben-Haim |
| 5,579,764 | A | 12/1996 | Goldrreyer |
| 5,588,432 | A | 12/1996 | Crowley |
| 5,662,108 | A | 9/1997 | Budd et al. |
| 5,687,737 | A | 11/1997 | Branham et al. |
| 5,713,946 | A | 2/1998 | Ben-Haim |
| 5,771,895 | A | 6/1998 | Slager |
| 5,840,031 | A | 11/1998 | Crowley |
| 6,019,725 | A | 2/2000 | Vesely et al. |
| 6,086,532 | A | 7/2000 | Panescu et al. |
| 6,102,863 | A | 8/2000 | Pflugrath et al. |
| 6,168,565 | B1 | 1/2001 | Napolitano |
| 6,200,269 | B1 | 3/2001 | Lin et al. |
| 6,216,027 | B1 | 4/2001 | Willis et al. |
| 6,246,898 | B1 | 6/2001 | Vesely et al. |
| 6,325,759 | B1 | 12/2001 | Pelissier |
| 6,389,311 | B1 | 5/2002 | Whayne et al. |
| 6,413,219 | B1 | 7/2002 | Avila et al. |
| 6,447,450 | B1 | 9/2002 | Olstad |
| 6,505,063 | B2 | 1/2003 | Van Den Brink et al. |
| 6,537,217 | B1 | 3/2003 | Bjaerum et al. |
| 6,546,279 | B1 | 4/2003 | Bova et al. |
| 6,575,901 | B2 | 6/2003 | Stoycos et al. |
| 6,650,927 | B1 | 11/2003 | Keidar |
| 6,679,847 | B1 | 1/2004 | Robinson et al. |
| 6,705,992 | B2 | 3/2004 | Gatzke |
| 6,728,562 | B1 | 4/2004 | Budd et al. |
| 6,950,689 | B1 | 9/2005 | Willis et al. |
| 7,263,397 | B2 | 8/2007 | Hauck et al. |
| 7,270,634 | B2 | 9/2007 | Scampini et al. |
| 7,285,117 | B2 | 10/2007 | Krueger et al. |
| 7,314,446 | B2 | 1/2008 | Byrd et al. |
| 7,415,169 | B2 | 8/2008 | Florent et al. |
| 7,485,115 | B2 | 2/2009 | Nakamura |
| 2003/0045795 | A1 | 3/2003 | Bjaerum et al. |
| 2003/0074011 | A1 | 4/2003 | Gilboa et al. |
| 2003/0120318 | A1 | 6/2003 | Hauck |
| 2003/0135115 | A1 | 7/2003 | Burdette et al. |
| 2003/0163045 | A1 | 8/2003 | Gatzke |
| 2003/0176778 | A1 | 9/2003 | Messing et al. |
| 2004/0097806 | A1 | 5/2004 | Hunter et al. |
| 2004/0127798 | A1 | 7/2004 | Dala-Krishna et al. |
| 2004/0147842 | A1 | 7/2004 | Desmarais |
| 2004/0152974 | A1 | 8/2004 | Solomon |
| 2004/0230111 | A1* | 11/2004 | Smith ...................... A61B 8/12 600/407 |
| 2004/0249259 | A1 | 12/2004 | Heimdal et al. |
| 2005/0033160 | A1 | 2/2005 | Yamagata et al. |
| 2005/0080336 | A1 | 4/2005 | Byrd et al. |
| 2005/0090745 | A1 | 4/2005 | Steen |
| 2005/0096543 | A1 | 5/2005 | Jackson et al. |
| 2005/0131474 | A1 | 6/2005 | Byrd et al. |
| 2005/0165279 | A1 | 7/2005 | Adler et al. |
| 2005/0171428 | A1 | 8/2005 | Fichtinger et al. |
| 2005/0203375 | A1 | 9/2005 | Willis et al. |
| 2005/0238253 | A1 | 10/2005 | Behrebbruch et al. |
| 2006/0036167 | A1* | 2/2006 | Shina ...................... A61B 6/12 600/433 |
| 2006/0041180 | A1 | 2/2006 | Viswanathan et al. |
| 2006/0182320 | A1 | 8/2006 | Peszynski et al. |
| 2006/0184016 | A1 | 8/2006 | Glossop |
| 2006/0229594 | A1 | 10/2006 | Francischelli et al. |
| 2006/0253030 | A1 | 11/2006 | Altmann et al. |
| 2006/0253031 | A1 | 11/2006 | Altman et al. |
| 2006/0253032 | A1 | 11/2006 | Altmen et al. |
| 2006/0287890 | A1 | 12/2006 | Stead et al. |
| 2007/0027390 | A1 | 2/2007 | Maschke et al. |
| 2007/0130287 | A1 | 6/2007 | Kumar et al. |
| 2007/0167801 | A1* | 7/2007 | Webler ................ G06F 19/3437 600/459 |
| 2007/0276243 | A1 | 11/2007 | Gerard et al. |
| 2007/0287902 | A1 | 12/2007 | Fuimaono et al. |
| 2008/0087833 | A1 | 4/2008 | McCroskey et al. |
| 2008/0146919 | A1 | 6/2008 | Camus et al. |
| 2008/0177994 | A1 | 7/2008 | Mayer |
| 2008/0199059 | A1 | 8/2008 | Eck et al. |

FOREIGN PATENT DOCUMENTS

| | | |
|---|---|---|
| EP | 1 465 540 B1 | 11/2008 |
| EP | 1 699 361 B1 | 9/2009 |
| JP | 2003-527880 A | 9/2003 |
| JP | 2005-510288 A | 4/2005 |
| JP | 2007-515242 A | 6/2007 |
| JP | 2007-536973 A | 12/2007 |
| WO | 92/19157 | 11/1992 |
| WO | 00/57767 | 10/2000 |
| WO | 01/20552 | 3/2001 |
| WO | 03/045263 A2 | 6/2003 |
| WO | 2005/063125 A1 | 7/2005 |
| WO | 2005/111932 A2 | 11/2005 |
| WO | 2006/076409 | 7/2006 |

OTHER PUBLICATIONS

Kapur et al., Combination of digital mammography with semi-automated 3D breast ultrasound, Technol Cancer Res Treat. Aug. 2004; 3(4): 325-334.*
Office Action dated Feb. 5, 2008; U.S. Appl. No. 11/182,910; filed Jul. 15, 2008; Applicant: Donaldson et al.; 10 pages.
Office Action dated Feb. 28, 2008; U.S. Appl. No. 11/433,951; filed May 15, 2006, Applicant: Donaldson; 11 pages.
Office Action dated Jan. 16, 2008; U.S. Appl. No. 11/162,473; filed Jul. 16, 2006: Applicant; Donaldson; 11 pages.
A. Milkowski et al. "Speckle Reduction Imaging"; Technical White Paper—General Electric Health Care (Ultrasound). Last accessed on Jul. 9, 2009. Available at http:www.gehealthcare.com/usen/ultrasound/education/docs/whitepaper_SRI.pdf.
http://medical.mernan-webster.com/medical/m-mode.
Radiology, vol. 121, 157-162. Copyright © 1976 by Radidogical Society of North America.
From Wire Reports. Scientists at Duke soon to begin testing 3-D ultrasound probe, Tue Sep. 2, 2008, (2) pgs.
L.F. Gutierrez, et al., Multimodality image guidance system integrating X-ray fluoroscopy and ultrasound image streams with electromagnetic tracking. Prog. in Biomedical Optics and Imaging—Proc of SPIE—Medical Imaging 2007: Visualization and Image-Guided Proc 2007 SPIE US, vol. 6509, No. Part 1, 2007, (10) pages.
Extended European Search Report, Application No. EP 09 16 9200.4-1265, dated Dec. 10, 2009, Applicant: General Electric Company, Reference No. 232716/14198, (11 pages).

* cited by examiner

METHOD AND APPARATUS FOR CATHETER GUIDANCE USING A COMBINATION OF ULTRASOUND AND X-RAY IMAGING

This application is a Divisional of U.S. patent application Ser. No. 12/205,599 entitled "Method and Apparatus for Catheter Guidance Using a Combination of Ultrasound and X-Ray Imaging" filed Sep. 5, 2008. The complete subject matter of which is incorporated herein by reference in its entirety.

BACKGROUND OF THE INVENTION

Field of the Invention

This invention relates generally to dual modality imaging and more particularly to vascular interventional radiology.

Vascular interventional radiology often involves angioplasty using a balloon catheter. Once in place, such as in an area of stenosis, the balloon is inflated, compressing the plaque against the walls of the vessel with the purpose of creating a larger lumen. Traditionally, fluoroscopy is used to track the insertion of a guide wire in real-time to an area in which the balloon catheter will be deployed. Vasculature is not visible on the fluoroscopic images, and thus a bolus of contrast is often injected through a guidance catheter to provide an image of the arterial tree. Precise guidance of the guide wire and catheter are needed to avoid damage to anatomical structures.

As the positioning of the guide wire involves real-time fluoroscopic imaging, the subject or patient typically receives a high dose of radiation over the course of the procedure, as do persons standing nearby. In addition, the contrast agent is quickly cleared by the body, and thus multiple doses of contrast are often injected, which in some cases may result in contrast induced nephrotoxicity, as well as additional cost.

BRIEF DESCRIPTION OF THE INVENTION

In one embodiment, an apparatus for tracking movement of a foreign object within a subject has an X-ray fluoroscopic system with an X-ray detector and an ultrasound system that has a probe with a position sensor. A display is configured to display a static X-ray image acquired by the X-ray fluoroscopic system and a real-time ultrasound image acquired by the ultrasound system. The X-ray image and the ultrasound image each display at least a portion of the foreign object and at least a portion of surrounding area. A tracking module is configured to track movement of the foreign object within the ultrasound image and the display is further configured to display an indication of the movement of the foreign object on the X-ray image.

In another embodiment, a method for positioning a guide wire within a subject comprises displaying a static X-ray image comprising at least a tip of a guide wire and vessels indicated by contrast. A live ultrasound image is displayed that includes at least the tip of the guide wire and at least a portion of the vessels. The guide wire is identified on both the X-ray image and the ultrasound image. Movement of the guide wire is indicated on the X-ray image based on movement of the guide wire that is detected in the ultrasound image.

In yet another embodiment, an apparatus for positioning a guide wire within the vasculature of a subject has an X-ray detector configured to detect X-rays that are generated by an X-ray tube and transmitted through a subject. An ultrasound probe has a position sensor. At least one display is configured to display a static contrast-enhanced X-ray image that is detected by the X-ray detector and a real-time ultrasound image that is acquired by the ultrasound probe. The X-ray image and the ultrasound image display at least a portion of a guide wire. A registration module is configured to register the X-ray and ultrasound images with respect to each other based on a point identified in each of the X-ray and ultrasound images. The display is further configured to display an indication of movement of the guide wire on the X-ray image based on movement of the guide wire detected within the ultrasound image.

DETAILED DESCRIPTION OF THE INVENTION

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Figure 1:
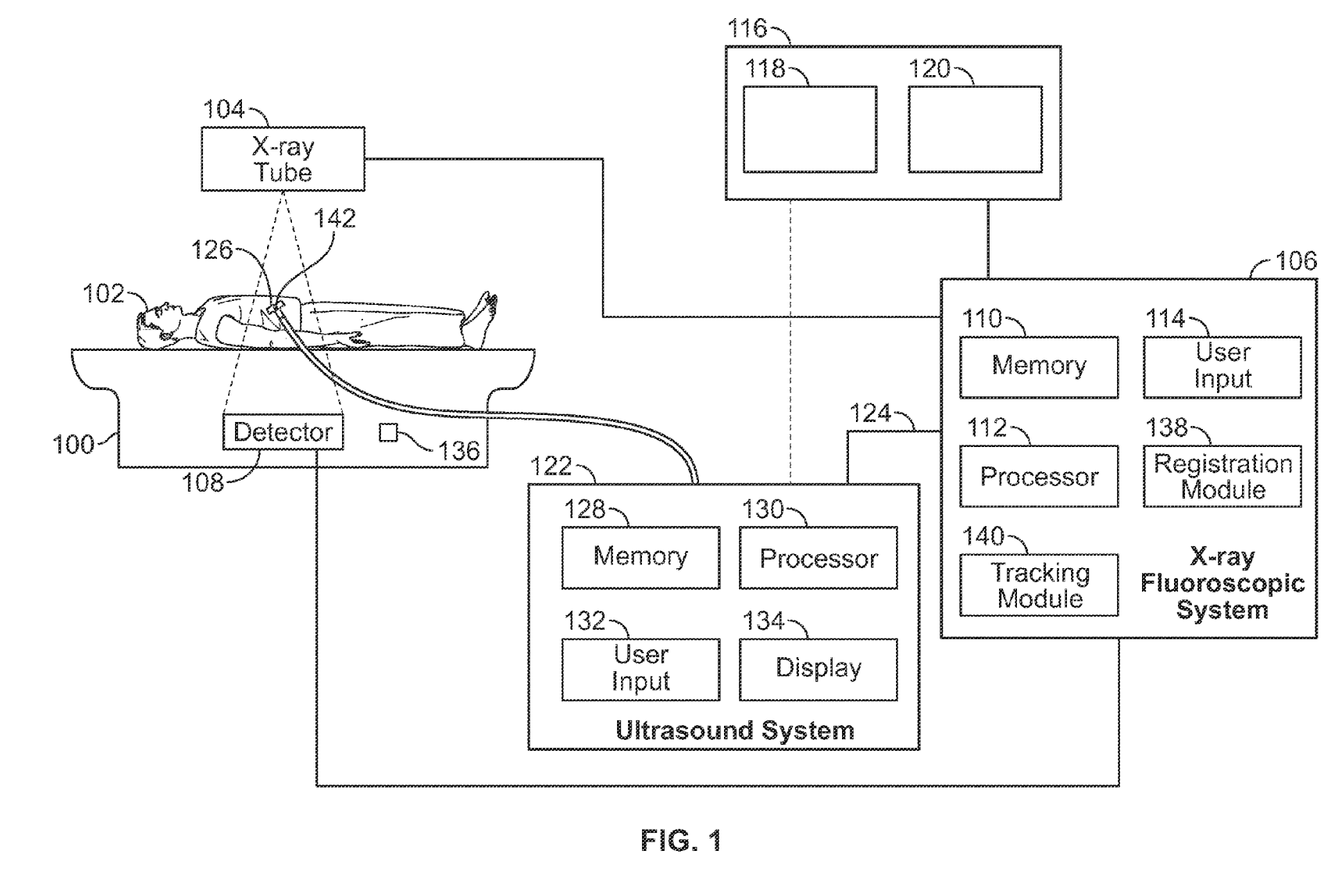
FIG. 1 illustrates an ultrasound system interconnected with an X-ray fluoroscopic system formed in accordance with an embodiment of the present invention.

FIG. 1 illustrates an ultrasound system interconnected with an X-ray fluoroscopic system in accordance with an embodiment of the present invention. A table 100 or bed is provided for supporting a subject 102. An X-ray tube 104 or other generator is connected to an X-ray fluoroscopic system 106. As shown, the X-ray tube 104 is positioned above the subject 102, but it should be understood that the X-ray tube 104 may be moved to other positions with respect to the subject 102. A detector 108 is positioned opposite the X-ray tube 104 with the subject 102 there-between. The detector 108 may be any known detector capable of detecting X-ray radiation.

The X-ray fluoroscopic system 106 has at least a memory 110, a processor 112 and at least one user input 114, such as a keyboard, trackball, pointer, touch panel, and the like. To acquire an X-ray image, the X-ray fluoroscopic system 106 causes the X-ray tube 104 to generate X-rays and the detector 108 detects an image. Fluoroscopy may be accomplished by activating the X-ray tube 104 continuously or at predetermined intervals while the detector 108 detects corresponding images. Detected image(s) may be displayed on a display 116 that may be configured to display a single image or more than one image at the same time.

An ultrasound system 122 communicates with the X-ray fluoroscopic system 106 via a connection 124. The connection 124 may be a wired or wireless connection. The ultrasound system 122 may transmit or convey ultrasound imaging data to the X-ray fluoroscopic system 106. The communication between the systems 106 and 122 may be one-way or two-way, allowing image data, commands and information to be transmitted between the two systems 106 and 122. The ultrasound system 122 may be a stand-alone system that may be moved from room to room, such as a cart-based system, hand-carried system, or other portable system.

An operator (not shown) may position an ultrasound probe 126 on the subject 102 to image an area of interest within the subject 102. The ultrasound probe 126 has a position sensor 142. The ultrasound system 122 has at least a memory 128, a processor 130, and a user input 132. Optionally, if the ultrasound system 122 is a stand-alone system, a display 134 may be provided. By way of example, images acquired using the X-ray fluoroscopic system 106 may be displayed as a first image 118 and images acquired using the ultrasound system 122 may be displayed as a second image 120 on the display 116, forming a dual display configuration. In another embodiment, two side-by-side monitors (not shown) may be used. The images acquired by both the X-ray fluoroscopic system 106 and the ultrasound system 122 may be acquired in known manners.

In one embodiment, the ultrasound system 122 may be a 3D-capable miniaturized ultrasound system that is connected to the X-ray fluoroscopic system 106 via the connection 124. As used herein, "miniaturized" means that the ultrasound system 122 is configured to be carried in a person's hand, pocket, briefcase-sized case, or backpack. For example, the ultrasound system 122 may be a hand-carried device having a size of a typical laptop computer, for instance, having dimensions of approximately 2.5 inches in depth, approximately 14 inches in width, and approximately 12 inches in height. The ultrasound system 122 may weigh about ten pounds, and thus is easily portable by the operator. An integrated display, such as the display 134, may be configured to display an ultrasound image as well as an X-ray image acquired by the X-ray fluoroscopic system 106.

As another example, the ultrasound system 122 may be a 3D capable pocket-sized ultrasound system. By way of example, the pocket-sized ultrasound system may be approximately 2 inches wide, approximately 4 inches in length, and approximately 0.5 inches in depth and weigh less than 3 ounces. The pocket-sized ultrasound system may include a display (e.g. the display 134), a user interface (e.g. user input 132) and an input/output (I/O) port for connection to the probe 126. It should be noted that the various embodiments may be implemented in connection with a miniaturized or pocket-sized ultrasound system having different dimensions, weights, and power consumption.

In another embodiment, the ultrasound system 122 may be a console-based ultrasound imaging system provided on a movable base. The console-based ultrasound imaging system may also be referred to as a cart-based system. An integrated display (e.g. the display 134) may be used to display the ultrasound image alone or simultaneously with the X-ray image as discussed herein.

In yet another embodiment, the X-ray fluoroscopic system 106 and the ultrasound system 122 may be integrated together and may share at least some processing, user input and memory functions. For example, a probe port 136 may be provided on the table 100 or other apparatus near the subject 102. The probe 126 may thus be connected to the probe port 136.

A registration module 138 may be used to register the first and second images 118 and 120 with respect to each other, and a tracking module 140 may be used to track a foreign object, such as a guide wire, within one of the images, which is a live image. The movement of the foreign object is indicated within a corresponding static image. In one example, the live image is an ultrasound image and the static image is an X-ray image. Although shown within the X-ray fluoroscopic system 106, the registration module 138 and the tracking module 140 may be within the ultrasound system 122 or within a separate module or system.

Figure 2:
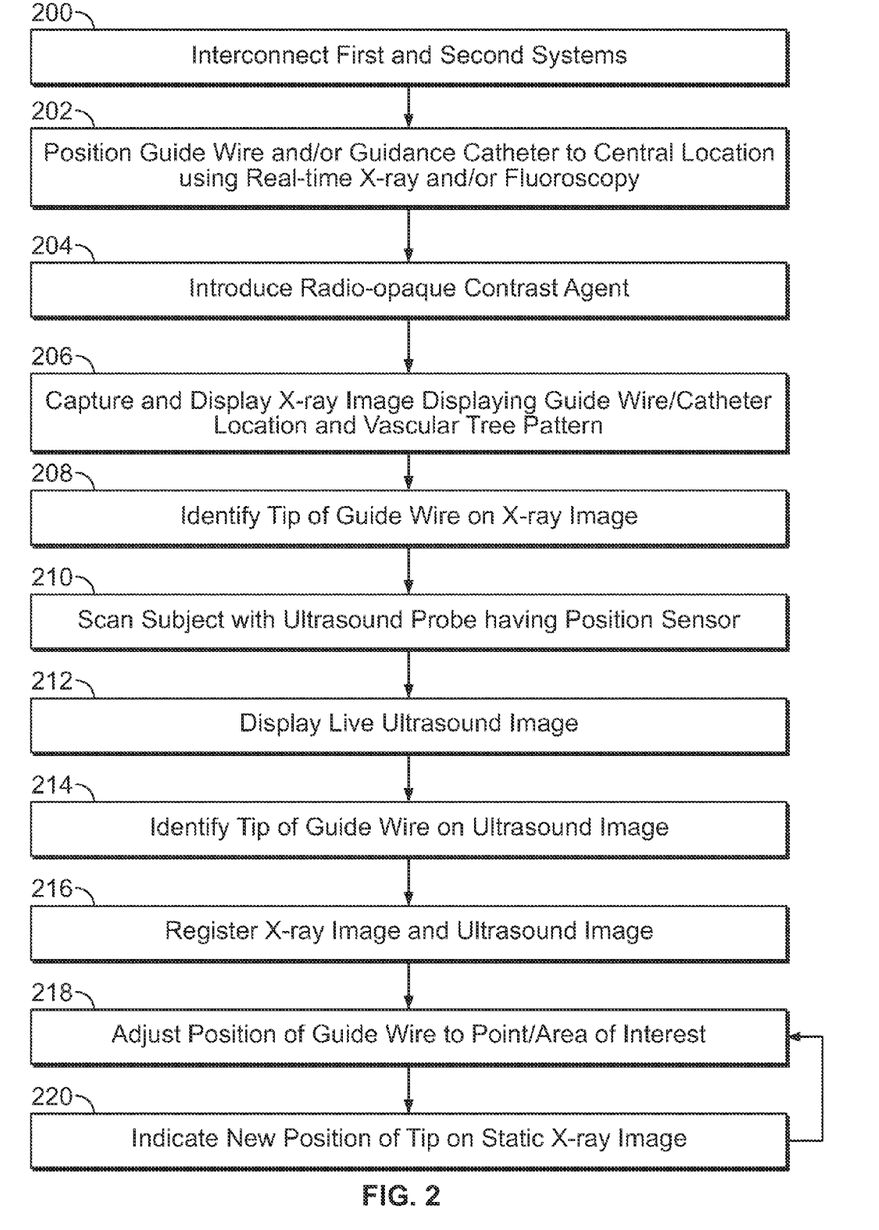
FIG. 2 illustrates a method for tracking movement of a foreign object on an image acquired by a first imaging system based on movement of the object within an image acquired by a second imaging system in accordance with an embodiment of the present invention.

FIG. 2 illustrates a method for tracking movement of a foreign object on an image acquired by a first imaging system based on movement of the object within an image acquired by a second imaging system. The foreign object may be any object inserted into the body such as a guide wire, a tip of the guide wire, or a catheter. In this example the two different imaging systems are the X-ray fluoroscopic system 106 and the ultrasound system 122, both shown in FIG. 1. In another embodiment, a different modality, such as a Magnetic Resonance Imaging (MRI) system or a Computer Tomography (CT) system may be used with the ultrasound system 122.

At 200, the first and second imaging systems are interconnected. For example, connection 124 may be used to connect the X-ray fluoroscopic system 106 and the ultrasound system 122 either through a wire or cable, or wirelessly. In another embodiment, if the two imaging systems are integrated into a single system, the probe 126 may be connected to the probe port 136.

At 202 real-time X-ray and/or fluoroscopy are used to provide images for initially positioning a guide wire and guidance catheter to a central location in the vascular system of the subject 102. The central location may be determined by the ultimate desired position of a balloon catheter or a position where other action is desired or needed. The fluoroscopic or X-ray images may be displayed as the first image 118 on the display 116.

When the tip of the guide wire has reached the desired initial position, at 204 a bolus of radio-opaque contrast agent is introduced through the guidance catheter. At 206, an X-ray image displaying the location of the guide wire and guidance catheter, as well as the vascular tree pattern, is captured and displayed on the display 116 as the first image 118. Therefore, the fluoroscopic image used when initially positioning the guide wire may be replaced on the display 116 by a contrast-enhanced X-ray image. By way of example, the contrast-enhanced X-ray image may be a single fluoroscopic frame, a single X-ray frame, or a digital subtraction angiographic image, where the resulting image is the difference between a pre-contrast and post-contrast injection image. It should be understood that other types of images may be used. In one embodiment, the ultimate desired position of the balloon catheter within the vascular system may be within the contrast-enhanced X-ray image.

Figure 3:
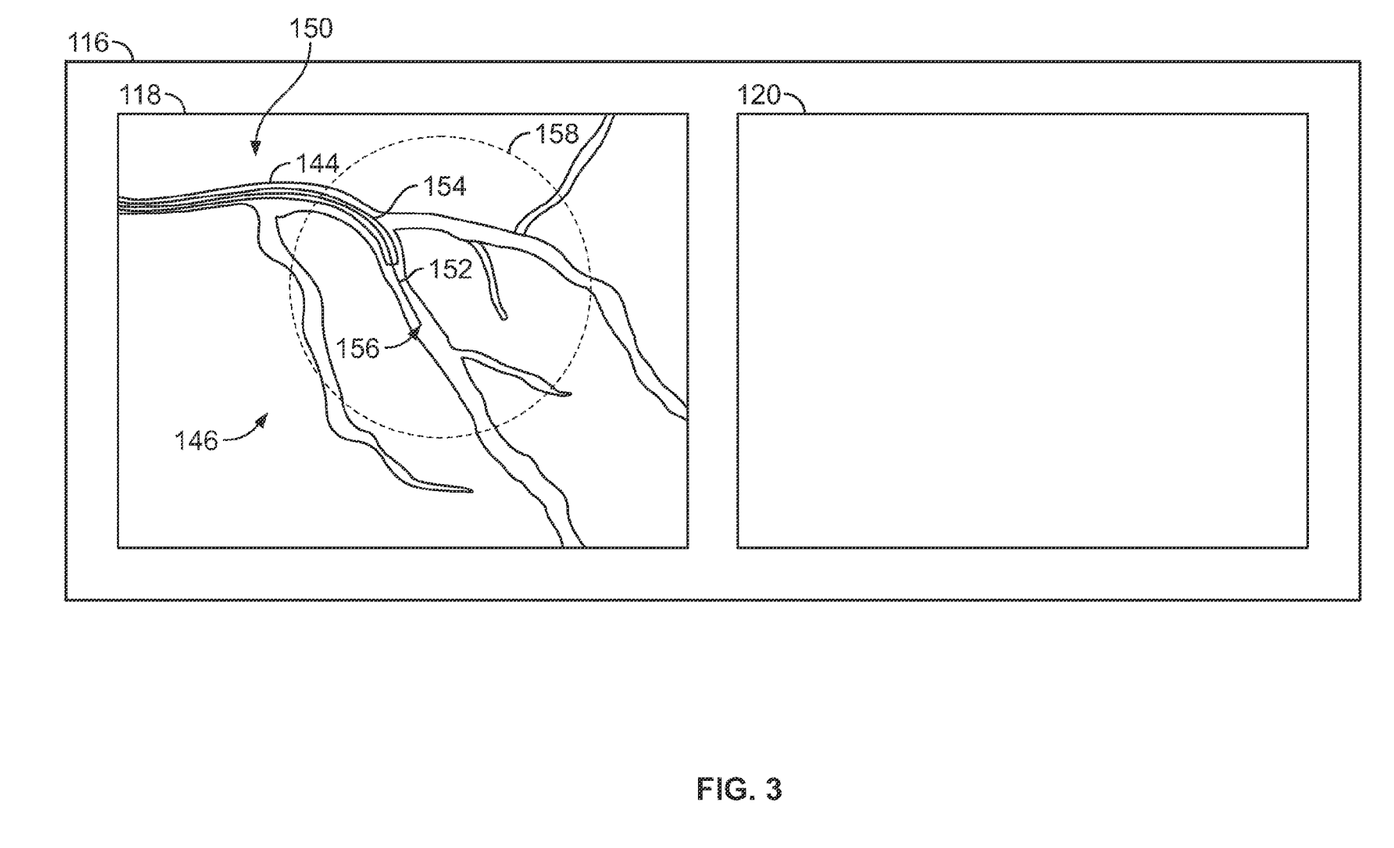
FIG. 3 illustrates a contrast-enhanced X-ray image on a display that shows the vascular tree pattern and a guide wire and guidance catheter inserted into a vessel in accordance with an embodiment of the present invention.

FIG. 3 illustrates a contrast-enhanced X-ray image 150 in accordance with an embodiment of the invention on the display 116 that shows a vascular tree pattern 146 as well as a guide wire 152 and a guidance catheter 154 inserted into a vessel 144. Returning to FIG. 2, at 208 a tip 156 (shown in FIG. 3) of the guide wire 152 is identified. The tip 156 may be the outermost end of the guide wire 152. For example, the operator may use the user input 114, such as a cursor, to select the tip 156. Alternatively, the processor 112 may automatically detect the tip 156 using, for example, boundary detection or other recognition type of algorithm that searches for the guide wire 152, or may detect the guide wire 152 based on a level of brightness in the X-ray image 150. Other automatic detection methods and algorithms may be used. In one embodiment, automatic detection may be accomplished within a user defined area or region of interest 158, while in another embodiment automatic detection may be accomplished across the entire X-ray image 150.

Figure 4:
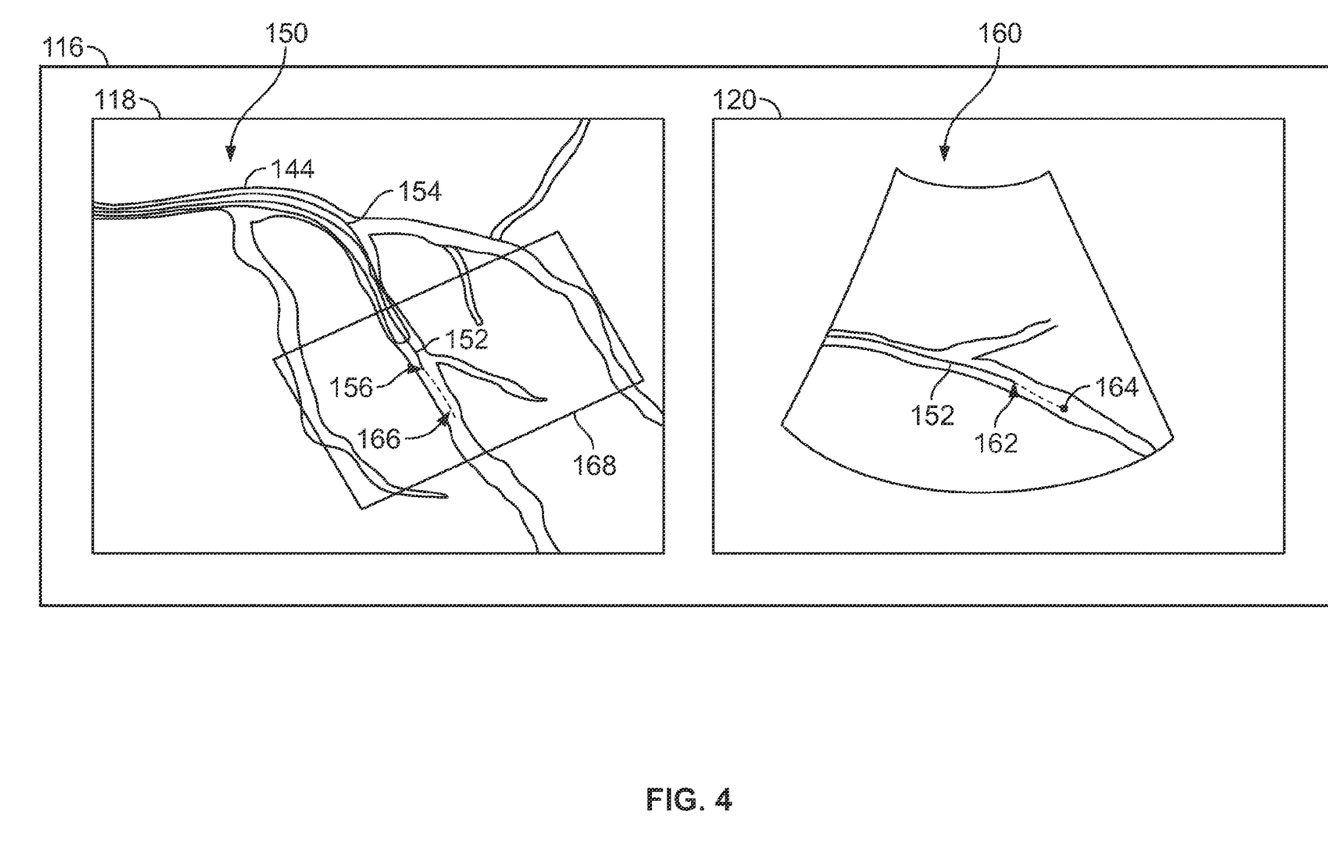
FIG. 4 illustrates the X-ray image and a real-time ultrasound image showing a guide wire in accordance with an embodiment of the present invention.

At 210 the operator scans the subject 102 with the ultrasound probe 126, and at 212 the live ultrasound image is displayed on the display 116 as the second image 120. FIG. 4 illustrates the X-ray image 150 and a real-time ultrasound image 160 showing the guide wire 152. By way of example only, the ultrasound image 160 may be a B-mode image. At 214 of FIG. 2, tip 162 (shown in FIG. 4) of the guide wire 152 is identified in the ultrasound image 160. The operator may identify the tip 162 using the one of the user inputs 114 or 132, or the tip 162 may be automatically identified through automatic image processing.

The X-ray image 150 has a fixed geometry based on the X-ray fluoroscopic system 106 that is known, and therefore the position and/or orientation of the guide wire 152 and tip 156 within the X-ray image 150 are also known. Using position information from the position sensor 142 of the probe 126 and the identified locations of the tips 156 and 162 in the images 150 and 160, at 216 the registration module 138 registers the X-ray image 150 and the ultrasound image 160 with respect to each other. Registration of the two images 150 and 160 may be accomplished using any registration process available for registering images acquired using two different modalities and/or two different imaging systems. For example, auto registration and correlation processes may be used based on anatomical similarities.

In another embodiment, an anatomical point that is visualized in both the X-ray image 150 and the ultrasound image 160 may be defined and/or selected, and may be used as the registration point. For example, the operator may select an intersection of two or more vessels on each of the images 150 and 160 and the registration module 138 may register the two images based on the two selected points.

The operator then, at 218, adjusts the position of the guide wire 152, feeding the guide wire 152 towards the point or area of interest. The operator may watch the motion of the guide wire 152 in real-time on the ultrasound image 160 while using the X-ray image 150 that shows the vascular tree pattern 146 as a base or reference image. The probe 126 may be moved or adjusted as necessary to view the anatomy of interest. In some embodiments, the tip 162 of the guide wire 152 may be indicated on the ultrasound image 160 with an indicator (not shown), and the processor 112 or 130 may automatically update the indicator as the tip 162 moves within the ultrasound image 160.

At 220 the tracking module 140 detects movement of the tip 162 of the guide wire 152 in the ultrasound image 160 and a new position of the corresponding tip 156 of the guide wire 152 is indicated on the X-ray image 150. For example, a position sensor (not shown) may be mounted to or integrated with the tip of the guide wire 152. The guide wire position sensor reading may be used to update the position on the X-ray image 150 as well as in the ultrasound image. In cases where the guide wire 152 is outside of the current ultrasound image, the position may be projected onto the ultrasound image with the relative location reflected in the graphical appearance of the projection. For example, the position sensor may transmit spatial location information wirelessly or through the guide wire 152. Alternatively, image processing and/or algorithms that may automatically identify the guide wire 152 in the ultrasound image 160, such as at 214, may be used to automatically track movement of the tip 162 of the guide wire 152. In another embodiment, after adjusting the guide wire 152 to a new location, the operator may identify the new location of the tip 162 on the ultrasound image 160 using one of the user inputs 114 or 132. The processor 112 and/or tracking module 140 then determine and indicate the corresponding location of the tip 156 on the X-ray image 150. It should be understood that other methods may be used to track, detect, and locate the position of the tip 162 of the guide wire 152 in the ultrasound image 160.

For example, the operator may advance the guide wire 152 to point 164 as shown on the ultrasound image 160 of FIG. 4. The movement of the guide wire 152 is indicated on the X-ray image 150 as dotted line 166. The indication on the display 116 may be a line, a dotted line, a dot, point, character such as an "X" or other indicator. In another embodiment, the indication may be displayed in a color or may have a different or predetermined intensity. In yet another embodiment, the indication may be a number that is used to indicate a location or to indicate movement based on time, distance, and the like, or any other indication that is visible to the operator so that the operator may track the real-time progress of the guide wire 152 on the static X-ray image 150.

The method loops between 218 and 220 to continuously detect (and possibly separately indicate) movement of the tip 162 of the guide wire 152 within the ultrasound image 160 and to indicate the movement of the corresponding tip 156 on the X-ray image 150. It should be understood that other foreign objects may be tracked and indicated in the same manner.

Once the tip 162 of the guide wire 152 is positioned in the desired region of the vessel, the operator may take further action based on the treatment or procedure. For example, the guidance catheter may be removed and a balloon catheter may be inserted using the guide wire 152 to position the balloon catheter, such as for angioplasty. Other interventional vascular procedures may be performed, such as ablation, biopsy and the like.

In one embodiment, a projection 168 (shown on FIG. 4) of the face of the probe 126 may be displayed on the X-ray image 150. The projection 168 is based on the particular probe 126 being used and thus may be a rectangle, as shown, a square or other shape. For example, the orientation of the probe 126 may be specified by the operator or the orientation of the probe face may be specified by using a fixed orientation during the specification of a common point, such as the tips 156 and 162. Alternatively, a graphic may be adjusted to match the current probe orientation, or the same point in the ultrasound image 160 may be marked from three or more probe face orientations. The projection 168 may be updated based on movement detected by the position sensor 142.

In some situations, the operator may wish to update the X-ray image 150 with a new subsequent X-ray image showing the vascular tree and the current position of the guide wire 152. The method may thus return to 204, wherein a new bolus of X-ray contrast agent is introduced. The subsequent x-ray image may replace the X-ray image 150. The tip 156 on the X-ray image 150 and optionally, the tip 162 on the ultrasound image 160, may be redefined, and the operator continues to advance the guide wire 152 as desired. Alternatively, the current guide wire indication(s) may be retained from the prior X-ray image(s).

In another embodiment, the operator may wish to update the X-ray image 150 to redefine the guide wire location without redefining or showing the vascular tree. In this example, a new contrast bolus is not used and thus a subsequent X-ray image is captured that does not display the vascular tree. The subsequent X-ray image may be fused with the X-ray image 150 to update the position of the guide wire 152. If multiple X-ray images are taken over time, multiple guide wires may be superimposed onto the same image. Each of the guide wires may be auto-detected and numbered (or otherwise indicated differently with respect to each other) to provide information regarding the most recent position as well as previous positions. Alternatively, the guide wire 152 may be removed or deleted from one or more previous images to display only the most recent guide wire 152 or to indicate the most recent position of the tip 156. In another embodiment, the guide wire indications may each be toggled on and off, such as to track the movement of the guide wire from one image to the next.

In some embodiments the ultrasound system 122 and probe 126 may be capable of real-time 3D imaging, also known as 4D imaging. The real-time 3D image data may be displayed on the display 116, such as in a volume, to allow real-time 3D tracking of the guide wire.

Figure 5:
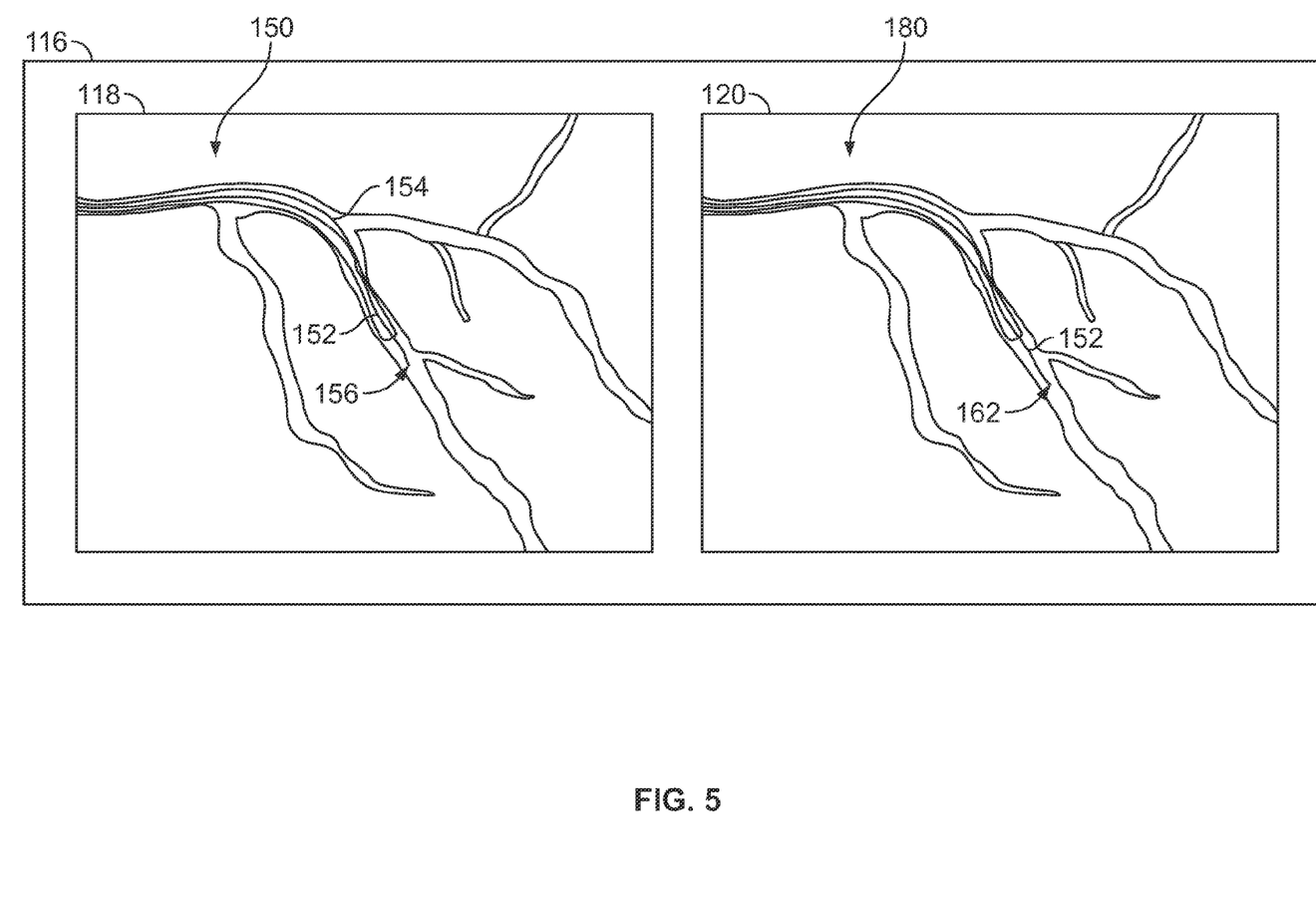
FIG. 5 illustrates the X-ray image and a real-time ultrasound projection image in accordance with an embodiment of the present invention.

The real-time 3D image data may also be displayed in any other 3D display method known in the art, such as maximum projection, average projection and surface rendering. FIG. 5 illustrates the X-ray image 150 and a real-time ultrasound projection image 180. The ultrasound system 122 collects real-time 3D imaging data, using a 3D capable probe that has the position sensor 142. As discussed previously, the operator selects the tip 156 on the X-ray image 150 and the tip 162 on the ultrasound image. Alternatively, one or both of the tips 156 and 162 may be automatically identified. The ultrasound image may be a B-mode ultrasound image 160 as previously discussed. The registration module 138 registers the two images with respect to each other, and the processor 112 forms an ultrasound projection image 180 that has the same orientation as the X-ray image 150.

In one embodiment, the projection image 180 is scaled geometrically to match the geometry of the X-ray image 150. In this example, processor 112 may automatically determine or the operator may input one or more anatomical landmarks or points that are used to determine scaling, and possibly orientation, of the images 150 and 180. The projection image 180 may then be combined with the X-ray image 150. For example, the projection image 180 may be fused with or overlaid on the X-ray image 150. Optionally, the X-ray image 150 may be overlaid on the projection image 180. The motion of the guide wire 152 may then be visually observed as the guide wire 152 and tip 162 move along the X-ray contrast opaque vessels. In a different embodiment, the projection image 180 is displayed separately from the X-ray image 150 as shown in FIG. 5, and the tracking module 140 tracks the movement of the guide wire 152 on the X-ray image 150 as discussed previously. In another embodiment, the display 116 may display more than two images, such that one or both of the X-ray and projection images 150 and 180 may be displayed simultaneously with a combined X-ray and projection image.

Other ultrasound images may be formed and displayed, such as a C-plane or other plane through the ultrasound volume. In the example of the C-plane, the probe 126 is positioned in the same orientation as the X-ray tube 104, such that the C-plane or slice is perpendicular to the direction of the X-rays. The C-plane may be oriented and scaled geometrically to match the X-ray image 150 orientation and dimensions, and may be overlaid on the X-ray image 150. The operator may then modify the depth of the C-plane that is displayed, allowing tracking of the movement of the guide wire 152 in the depth direction. If displaying a plane that is not the C-plane, the operator may adjust the position of the plane, but this may not correlate with the depth as defined by the orientation of the X-ray image 150. As with the ultrasound projection image 180, the C-plane or other plane may be displayed simultaneously with the X-ray image 150 and/or simultaneously with an image that combines the X-ray image 150 and the ultrasound plane.

In another embodiment, the ultrasound system 122 may acquire 2D ultrasound image data. Alternatively, a slice or plane of 2D ultrasound data may be selected from an acquired ultrasound volume. The 2D dataset may be overlaid, fused or otherwise combined with the X-ray image 150 (or the X-ray image 150 may be overlaid on the 2D dataset) and displayed on the display 116 as a single image.

In addition to tracking the guide wire 152, the ultrasound system 122 may be used to evaluate a procedure immediately, such as immediately post-angioplasty, to non-invasively document the absence of a flow reducing stenosis or to identify additional areas of concern. For example, B-mode, color and spectral Doppler modes and the like may be used. Also, the use of the ultrasound system 122 may lead to less mistakes in the navigation of the guide wire 152.

In another embodiment, once the guide wire 152 has been advanced to the initial position, such as at 202 of FIG. 2, ultrasound contrast agent may be introduced into the subject 102. A 3D ultrasound vascular image may then be acquired and used as the base or reference image rather than the contrast-enhanced X-ray image 150. The ultrasound vascular image may be, for example, a rendered ultrasound image of the contrast agent or a projection image, and is used together with the live ultrasound image 160 for guidance of the guide wire 152.

A technical effect of at least one embodiment is the ability to guide the movement and placement of a guide wire and/or catheter or other foreign object using two imaging modalities at the same time. One imaging modality may be X-ray fluoroscopy in which a bolus of contrast agent is introduced so that the vascular tree may be imaged and displayed. The other imaging modality may be ultrasound wherein the static contrast-enhanced X-ray image and the real-time ultrasound image are registered with respect to each other. The operator may then utilize both the X-ray image and the real-time ultrasound image to advance the guide wire. The amount of contrast that needs to be given to the subject may be decreased, thus decreasing the possible side effects of the contrast, such as nephrotoxicity. Also, because fluoroscopy is not being continuously performed throughout the procedure, the operator, subject and other staff receive less X-ray radiation compared to procedures conducted using only X-ray.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for positioning a guide wire within a subject during a procedure, the method comprising:
    capturing and displaying a single static X-ray image comprising at least a tip of a guide wire and a vascular tree pattern of vessels indicated by contrast;
    utilizing an ultrasound system to collect real-time live ultrasound images throughout at least a portion of the procedure;
    displaying the live ultrasound images comprising at least the tip of the guide wire and at least a portion of the vessels to show motion of the guide wire in real time on the live ultrasound images throughout at least the portion of the procedure;
    registering the single static X-ray image with the live ultrasound images;
    identifying the guide wire on both the single static X-ray image and the ultrasound image;
    automatically detecting movement of the guide wire within the live ultrasound images throughout at least the portion of the procedure based on automatic image processing of the live ultrasound images; and
    presenting, on the single static X-ray image throughout at least the portion of the procedure, an indication of movement of the guide wire within the vascular tree pattern, wherein the indication of movement is based on the movement of the guide wire automatically detected within the live ultrasound images.

2. The method of claim 1, further comprising:
    receiving inputs associated with the single static X-ray image and the live ultrasound images; and
    registering the single static X-ray and ultrasound images based on the inputs.

3. The method of claim 1, the identifying further comprising identifying a region of interest associated with the single static X-ray image, the method comprising automatically detecting the tip of the guide wire within the region of interest.

4. The method of claim 1, further comprising displaying the single static X-ray image and the live ultrasound images simultaneously on one of a single display and two displays positioned side-by-side.

5. The method of claim 1, wherein live the ultrasound images comprise one of projection images, a 2D dataset and a 3D dataset, the method further comprising:
    combining the live ultrasound images and the single static X-ray image to form a combined image; and
    displaying at least the combined image.

6. The method of claim 1, wherein the live ultrasound images are plane representative of ultrasound data from within a 3D volume of data, the method further comprising at least one of displaying the plane overlaid on the single static X-ray image and displaying the plane simultaneously with the single static X-ray image.

7. The method of claim 1, further comprising:
    acquiring a subsequent X-ray image, the subsequent X-ray image displaying at least the tip of the guide wire; and
    combining the subsequent X-ray image and the single static X-ray image to display a new position of the tip of the guide wire.

8. The method of claim 1, further comprising:
    acquiring at least one subsequent X-ray image, the at least one subsequent X-ray image displaying the guide wire;
    deleting the guide wire on the single static X-ray image; and
    combining the subsequent X-ray image and the single static X-ray image.

9. The method of claim 1, wherein the automatically detecting operation obtains tip movement information for the tip of the guide wire based on automatic image processing of the ultrasound images, the method further comprising automatically updating the indicator as the tip of the guide wire moves within the live ultrasound images based on the tip movement information.

10. The method of claim 1, wherein the guide wire is identified by one of automatically or manually identifying the tip of the guide wire in the single static X-ray image and in a first image from the live ultrasound images.

11. The method of claim 1, wherein the registering operation includes registering the single static X-ray image with a first image from the live ultrasound images based on i) position information from a position sensor on a probe of the ultrasound system and ii) the identification of the tip of the guide wire in the single static X-ray image and the first image.

12. The method of claim 1, wherein the indication is presented on the single static X-ray image as at least one of a line, a dotted line, a dot, a point, character, color, number and predetermined intensity.

13. The method of claim 1, wherein the ultrasound system collects real-time 3-D imaging data, the method further comprising forming ultrasound projection images having a same orientation as the single static X-ray image, the ultrasound projection images being displayed as the live ultrasound images.

14. The method of claim 1, further comprising forming C-plane images as the live ultrasound images, the displaying operation displaying the C-plane images oriented an scaled geometrically to match and orientation and dimensions of the single static X-ray image.

15. The method of claim 14, further comprising modifying a depth of the C-plane corresponding to the C-plane images displayed to allow tracking of the movement of the guide wire in a depth direction.

16. The method of claim 1, wherein the presenting operation includes a visually presenting motion of the guide wire along the single static X-ray image within the vascular tree pattern.

17. The method of claim 1, wherein the automatically detecting operation performs automatic image processing of multiple ultrasound images to continuously detect movement of a tip of the guide wire.

18. The method of claim 1, further comprising forming an ultrasound projection image based on the live ultrasound images, where the ultrasound projection image has a same orientation as the single static x-ray image, the ultrasound projection image and the single static x-ray image being co-displayed.

19. The method of claim 18, further comprising scaling a geometry of the ultrasound projection image to match a geometry of the single static x-ray image.

20. The method of claim 1, wherein the live ultrasound image represents a C-plane image that is oriented and scaled geometrically to match and orientation and dimensions of the single static x-ray image.

* * * * *